United States Patent
Spangelo et al.

(10) Patent No.: US 8,703,756 B2
(45) Date of Patent: Apr. 22, 2014

(54) SYNTHETIC PROCEDURE AND CANCER TREATMENT WITH CISPLATIN DERIVATIVES

(75) Inventors: Bryan L. Spangelo, Henderson, NV (US); Van Vo, Las Vegas, NV (US); Pradip K. Bhowmik, Henderson, NV (US); Ontida Tanthmanatham, Las Vegas, NV (US); Haesook Han, Henderson, NV (US)

(73) Assignee: The Board of Regents of the Nevada System of Higher Education on Behalf of the University of Nevada, Las Vegas, Las Vegas, NV (US)

( * ) Notice: Subject to any disclaimer, the term of this patent is extended or adjusted under 35 U.S.C. 154(b) by 238 days.

(21) Appl. No.: 13/404,257

(22) Filed: Feb. 24, 2012

(65) Prior Publication Data

US 2013/0225546 A1    Aug. 29, 2013

(51) Int. Cl.
*A61K 31/555* (2006.01)
*C07F 15/00* (2006.01)

(52) U.S. Cl.
USPC .............................. 514/188; 546/2

(58) Field of Classification Search
USPC .............................. 514/188; 546/2
See application file for complete search history.

(56) References Cited

PUBLICATIONS

Blight, B.A. et al.: Stability of Pseudotaxanes templated through second-sphere coordination. Inorganic Chem. vol. 48, pp. 1920-1927, 2009.*
Culine et al., Docetaxel and Cisplatin in Patients With Metastatic Androgen Independent Prostate Cancer and Circulating Neuroendocrine Markers, The Journal of Urology, Sep. 2007, pp. 844-848, vol. 178, USA. Copyright 2007 by American Urological Association. DOI:10.1016/j.juro.2007.05.004 (5 pages).
Dhar et al., Targeted delivery of cisplatin to prostate cancer cells by aptamer functionalized Pt(IV) prodrug-PLGA-PEG nanoparticles, PNAS, website: www.pnas.org/cgi/doi/10.1073/pnas.0809154105, Nov. 11, 2008, pp. 17356-17361, vol. 15, No. 45, copyright 2008 by The National Academy of Sciences of the USA. (15 pages).
Gong et al., Kindlin-2 controls sensitivity of prostate cancer cells to cisplatin-induced cell death, Cancer Letters homepage: www.elsevier.com/locate/canlet, 2010, pp. 54-62, vol. 299, Copyright 2010 Elsevier Ireland Ltd. (9 pages).
Buonerba et al., Phase II trial cisplatin plus prednisone in docetaxel-refractory castration-resistant prostate cancer patients, Cancer Chemother Pharmacol Clinical Trial Report, Department of Endocrinology and Medical Onocology, Genitourinary Cancer Section, University of Federico II, Naples, Italy, Mar. 2, 2011, pp. 1455-1461, (2011) 67:1455-1461, DOI 10.1007/s00280-011-1594-z, Copyright Springer-Verlag 2011 Italy (7 pages).

Dhar et al., Targeted delivery of a cisplatin prodrug for safer and more effective prostate cancer therapy in vivo, PNAS Early Edition, website: www.pnas.org/cgi/doi/10.1073/pnas.1011379108, Aug. 1, 2010, pp. 1-7, USA. (7 pages).
Vesprini et al., The therapeutic ratio is preserved for radiotherapy or cisplatin treatment in BRCA2-mutated prostate cancers, CUAJ, Apr. 2011, pp. E31-E35, vol. 5, Issue 2, © 2011 Canadian Urological Association (5 pages).
Nagourney et al., Gemcitabine Plus Cisplatin Repeating Doublet Therapy in Previously Treated, Relapsed Breast Cancer Patients, Journal of Clinical Oncology, vol. 18, No. 11 (Jun. 2000): pp. 2245-2249. American Society of Clinical Oncology. (5 pages).
Koshy et al., Cisplatin-gemcitabine therapy in metastatic breast cancer: Improved outcome in triple negative breast cancer patients compared to non-triple negative patients, Elsevier Journal Homepage www.elsevier.com/brst, The Breast 19 (2010) pp. 246-248. (8 pages).
Silver et al., Efficacy of Neoadjuvant Cisplatin in Triple-Negative Breast Cancer, Journal of Clinical Onocology, Mar. 1, 2010, pp. 1145-1153, vol. 28, No. 7, Copyright 2010 American Society of Clinical Onocology. (9 pages).
Westmose et al., Enhancing cicplatin sensitivity in MCF-7 human breast cancer cells by down-regulation of Bcl-2 and cyclin D1, International Journal of Onocology, Jul. 25, 2006, pp. 1397-1404, vol. 29, Institute of Biochemistry and Molecular Biology, Iniversity of Southern Denmark, Odense, Denmark. (8 pages).
Abratt et al., Chemotherapy for metastatic non-small cell lung cancer, S Afr Med J, Feb. 3, 1990, pp. 161-162, vol. 77, Department of Radiotherapy, Groote Schuur Hospital Observatory, 7925 RSA. (2 pages).
Azzoli et al., Cisplatin Versus Carboplatin for Patients with Metastatic Non-Small-Cell Lung Cancer—An Old Rivalry Renewed, Editorials JNCI, Jun. 6, 2007, vol. 99, Issue 11 pp. 828-829, published by Oxford University Press Copyright 2007. (2 pages).
Tiseo et al., Cisplain or carboplatin in the treatment of non-small cell lung cancer: a comprehensive review, Oncol Review, Oct. 31, 2007, pp. 162-169, Division of Medical Onocology, University of Parma, Italy. (8 pages).
Douillard et al., Adjuvant Cisplatin and Vinorelbine for Completely Resected Non-small Cell Lung Cancer—Subgroup Analysis of the Lung Adjuvant Cisplatin Evaluation, Journal of Thoracic Onocology, Feb. 2010, pp. 220-234, vol. 5, No. 2, Copyright 2010 for the International Association for the Study of Lung Cancer, France. (12 pages).

(Continued)

*Primary Examiner* — Charanjit Aulakh
(74) *Attorney, Agent, or Firm* — Fish & Richardson P.C.

(57) ABSTRACT

A method of reducing the in vivo viability of cancer cells selected from the group consisting of breast cancer cells, lung cancer cells, prostate cancer cells and melanoma cancer cells has steps of:
  a) identifying a prospective patient having cancer cells selected from the group consisting of breast cancer cells, lung cancer cells, prostate cancer cells and melanoma cancer cells; and
  b) administering a cisplatin derivative to the prospective patient so that the cisplatin derivative will contact the cancer cells;
wherein the cisplatin derivative is a 4,4'-bis[RO]-2,2'-bipyridine)PtCl$_2$ where, R is selected from the group consisting of —(CH$_2$)$_n$CH3 where n=2, 3, 4 or 5, and —(CH$_2$)$_n$[O(CH$_2$)$_m$]$_y$O(CH$_2$)$_z$CH$_3$ where n=2, m=2, y=2, z=1. A novel synthetic process for the manufacture of these compounds (and their analogs) is also provided.

17 Claims, 15 Drawing Sheets

(56) References Cited

PUBLICATIONS

Oliver et al., Chronic Cisplatin tratment promotes enhanced damage repair and tumor proession in a mouse model of lung cancer, www.genesdev.cship.org (downloaded Feb. 1, 2012), Genes & Development 24:837-852, Copyright 2010, Published Mar. 1, 2010, by Cold Spring Harbor Laboratory Press, USA. (17 pages).

Pectasides et al., Treatment o metastatic malignant melanoma with decarbazine, vindesine and cisplatin, Br. J. Cancer, 1989, 60, pp. 627-629, First Department of Medical Onocology, The Metaxas Memorial Cancer Hospital, Piraeus, Greece, Copyright The Macmillan Press Ltd., 1989. (3 pages).

Legha et al., Treatment of metastatic melanoma with combined chemotherapy containing cisplatin, vinblastine and dacarbazine (CVD) and biotherapy using interleukin-2 and interferon-a, Annals of Onocology 7, pp. 827-835, 1996, Copyright 1996 Kluwer Academic Publishers, Printed in the Netherlands. (9 pages).

Blesa et al., Treatment options for metastatic melanoma. A systematic review, Cancer Therapy, Published Apr. 2009, pp. 188-198, vol. 7, Spain. (9 pages).

Eager et al., Phase II assessment of talabostat and cisplatin in second-line stage IV melanoma, BioMed Central, Jul. 30, 2009, Published Jul. 30, 2009, Copyright 2009 Eager et al; licenses BioMed Central Ltd. available from http://www.biomedcentral.com/1471-2407/9/263 , Texas, USA. (11 pages).

Shimabukuro et al., DNA damage and repair in leukocytes of melanoma patients exposed in vitro to cisplatin, Oct. 13, 2010, 2011 Melanoma Research, 0960-8931, vol. 21, No. 2, Copyright 2011 Wolters Kluwer Health, Lippincott illiams, Wilkins. University of So Paulo, Brazil. (7 pages).

\* cited by examiner

Figure 12

Table 1

| Compound | EC$_{50}$ (μM) for 1 h treatment |
|---|---|
| CDDP | > 1000 |
| Carboplatin | > 1000 |
| R = CH$_3$ | >100 |
| R = CH$_2$CH$_3$ | >100 |
| R = (CH$_2$)$_2$CH$_3$ | 48 ± 3 |
| R = (CH$_2$)$_3$CH$_3$ | 17 ± 1 |
| R = (CH$_2$)$_4$CH$_3$ | 18 ± 1 |
| R = (CH$_2$)$_5$CH$_3$ | 66 ± 16 |
| R = CH$_2$CH$_2$OCH$_3$ | >100 |
| R = (CH$_2$CH$_2$O)$_2$CH$_2$CH$_3$ | >200 |
| R = (CH$_2$CH$_2$O)$_3$CH$_2$CH$_3$ | >1000 |

Figure 13

Table 2

| Compound | $EC_{50}$ (μM) for 48 h treatment |
|---|---|
| CDDP | > 1000 |
| R = $CH_3$ | >100 |
| R = $CH_2CH_3$ | 66 ± 7 |
| R = $(CH_2)_2CH_3$ | 17 ± 1 |
| R = $(CH_2)_3CH_3$ | 15.4 ± 0.5 |
| R = $(CH_2)_4CH_3$ | 16.5 ± 0.5 |
| R = $(CH_2)_5CH_3$ | 19.1 ± 0.8 |
| R = $CH_2CH_2OCH_3$ | >100 |
| R = $(CH_2CH_2O)_2CH_2CH_3$ | >200 |
| R = $(CH_2CH_2O)_3CH_2CH_3$ | 730 ± 56 |

Figure 14

Table 3

| Cell line | CDDP | R = (CH$_2$)$_3$CH$_3$ |
|---|---|---|
| DU-145 | >1000 | 8 ± 2 |
| MDA-MB-435 | >1000 | 3.3 ± 0.4 |
| MCF7 | >1000 | 32 ± 5 |
| T-47D | >1000 | 14 ± 2 |
| HCC38 | >1000 | 5 ± 1 |
| MDA-MB-231 | >1000 | 12 ± 3 |

SYNTHETIC PROCEDURE AND CANCER TREATMENT WITH CISPLATIN DERIVATIVES

BACKGROUND OF THE INVENTION

1. Field of the Invention

The present invention relates to the synthesis of and use of classes of compounds in the treatment of disease, including cancer. A narrow class of analogs of cisplatin has been found to display significantly improved results against a number of types and lines of cancer as compared to closely related analogs.

2. Background of the Art

Cancer is currently the second leading cause of death in the United States, accounting for nearly one-quarter of the deaths. One in two men and one in three women will develop some type of cancer within their lifetime. The American Cancer Society estimated about 1.6 million new cases of cancer in 2012. With such alarming figures, many researchers are working towards the development of new or better treatment for cancer.

Cisplatin (CDDP), approved for clinical treatment by the Food and Drug Administration (FDA) in 1978, belongs to a family of platinum-containing compounds used in the treatment of various types of cancers such as bladder, ovarian, and testicular cancers. While effective as an antitumor agent, its application is limited due to toxic side effects; especially nephrotoxicity. As a consequent of the limitations of cisplatin, numerous analogues have been developed and studied with the goal of finding compounds that could be more effective and possess less toxicity. In 1989, carboplatin was the first cisplatin analogue approved by the FDA for the treatment of lung and ovarian cancer. Oxaliplatin became the third platinum (Pt)-containing compound approved by the FDA in 2002 for the treatment of colorectal cancer. Although carboplatin and oxaliplatin are less toxic than cisplatin, they are either only as effective as or in many cases less effective than cisplatin. Additionally, these analogues also have dose limiting side effects such as myelosuppression. Thus, the search for improved drugs continues.

U.S. Pat. No. 4,177,263 describes various methods for utilizing cisplatin and cisplatin analogs of Pt(II) or Pt(IV) containing various amine and chloro groups to treat tumor cells. It was demonstrated that mouse tumors and leukemia were successfully treated with the described compounds. Although cisplatin was shown to be effective in this patent and is currently used in clinical treatment of various tumors, it has drawbacks such as dose limiting side effects and development of resistance. Additionally, results from our experiments indicate that the novel platinum complexes in this invention are much more potent than cisplatin.

U.S. Pat. No. 4,584,316 describes the synthesis and use of palladium complexes as anti-tumor agents. Of relevance to our invention is the incorporation of the 2,2'-bipyridine ligand in the complex of the formula Pd(II)(cis-2,2'-bipyridine)$(NO_3)_2$. This complex gave a percent increased life span (% ILS) of 55-70 when tested on mice; the result is comparable to that of cisplatin which gave a % ILS of 65-80. The compounds were not found to be more effective than cisplatin.

It is known that numerous transition metal complexes, particularly palladium and platinum complexes, have chemotherapeutic activity, as described in U.S. Pat. No. 4,584,316. However, the compounds used at present have a therapeutic index (efficacy/toxicity ratio) which is still too low. Their excessive toxicity limits their use, notably on account of the risk of renal lesions. One way of reducing this major disadvantage is to "isolate" these complexes by incorporation into or association with a vector, permitting a slower diffusion of the active principal. The encapsulation into liposomes of cis-platinum (Freise, J., W. H. Mueller, P. Magerstedt, H. J. Schmoll (1982) Arch. Int. Pharmacodyn., 258, 180) and analogs thereof (Khokhar, A. R., S. Al-Baker, R. Perez-Soler (1988) Anticancer Drug Design 3, 177), reduces the efficacy of these agents, but improves the therapeutic index, prolongs their action, favorably modifies their biodistribution, and even promotes the induction of an antitumor activity against resistant tumors.

Cisplatin (cis-diamminedichloroplatinum, cis-Pt$(NH_3)_2$$Cl_2$, molecular weight 300.05) has been used as a chemotherapeutic agent for many years since the discovery of its anti-tumor activity by B. Rosenberg et. al. (Nature, 1965, 205, 698; Nature, 1972, 222, 385).

Chemical & Engineering News (Oct. 23, 1995) reported that "Cisplatin was first synthesized in the 1800s, but its anticancer activity was not discovered until the 1960s. In 1979, it was approved by the Food and Drug Administration for clinical treatment of testicular and ovarian tumors and cancers of the head and neck. Cisplatin and an analog, carboplatin, are now among the most widely used anticancer drugs."

The Physician's Desk Reference reports that cisplatin (the commercial name is Platinol®) can be used to treat testicular cancer, ovarian cancer, and bladder cancer. Rosenberg et al., U.S. Pat. No. 4,177,263, describes methods of treating cancer using cisplatin and cisplatin analogs.

The compound was shown to be effective for treating leukemia and tumors induced in mice. After so many years, cisplatin is still being widely used because of its efficacy. However, its critical drawback, the toxicity, is still a major concern. Many attempts have been made to either reduce its toxicity or increase its efficacy.

Predominantly, cisplatin binds onto deoxyguanosine of DNA. It also binds onto other deoxynucleosides or nucleosides. Because of the non-selectivity of cisplatin between cancer cells and normal cells, cisplatin has numerous side effects. Besides, cisplatin is effective only to certain kinds of cancers. Therefore, reducing the toxicity of cisplatin and expanding its use in more cancers have been very important issues for all scientists involved in its research.

Many people have attempted to change the ligand on platinum to make new cisplatin analogs in order to reduce the toxicity or improve the efficacy. Examples are made by K. C. Tsou, et al. (J. Clin. Hemat. Oncol. 1977, 7, 322), R. J. Speeder et al. (J. Clin. Hemat. Oncol. 1977, 7, 210), A. Mathew et. al. (Chem. Comm. 1979, 222), D. Rose, et al. (Cancer Treatment Reviews, 1985, 12, 1), and D. Alberts et al. (Cancer Treatment Reviews, 1985, 12, 83).

U.S. Pat. Nos. 5,648,362 and 5,399,694, describe the synthesis and use of, in addition to other complexes, platinum complexes containing 4,4'-substituted-2,2'-bipyridine. The substituents may be —$WR^1$ at the 4 position and —$WR^2$ at the 4' position or —$WR^2$ at the 4 position with —$WR^1$ at the 4' position. W can be a methylene, ether, carbonyl, ester, or amide group. $R^1$ contains both a hydrocarbon substituent and a fluoroalkylated substituent; $R^2$ consists of a hydrogen or a hydrocarbon chain. These amphiphilic, fluoroalkylated complexes are to be used when incorporated into liposomes or as emulsions composed of an oily phase, an aqueous phase, and a surfactant. The described invention has drawbacks such as for the synthesis of compounds where W is a methylene; a strong base such as lithium diisopropylamide (LDA) is needed to deprotonate the starting 4,4'-dimethyl-2,2'-bipyridine. LDA is inconvenient as it reacts violently with water;

thus, reactions must be performed in specialized glassware under argon or nitrogen. Additionally, if not handled properly, LDA catches fire spontaneously if exposed to air and can release flammable gases which may in turn ignite spontaneously if exposed to water. Another deficiency of the invention is that based on the in vitro results presented most of the synthesized compounds when incorporated into liposomes are less effective than non-encapsulated cisplatin and only one compound had activity close to that of the non-encapsulated cisplatin.

U.S. patent application Ser. No. 11/400,886 describes the synthesis and use of platinum complexes having the formula cis-LPtCl$_2$ (L=4,4'-substituted-2,2'-bipyridine or 4,7-substituted-1,10-phenanthroline) for the treatment of cancer. The substituents are alkyl groups that may include "normal, branched and cyclic alkyl groups, alkyl groups with ether linkages, highly fluorinated alkyl group, highly fluorinated alkyl groups with ether linkages, hydroxyl terminated alkyl groups, hydroxyl-terminated alkyl groups with ether linkages and perfluorinated alkyl groups." The complexes of this invention are similar to complexes described in U.S. Pat. Nos. 5,648,362 and 5,399,694; however, the complexes do not necessarily have to contain fluorine atoms. Furthermore, manipulation of the compounds is by a suspension or dissolved solution without incorporation into lipids or liposomes. Similar to U.S. Pat. Nos. 5,648,362 and 5,399,694, synthesis of the ligands of U.S. patent application Ser. No. 11/400,886 requires the use of LDA to deprotonate the starting 4,4'-dimethyl-2,2'-bipyridine. As mentioned previously LDA is difficult to work with because of its extreme reactivity with water. Additionally, LDA is a known teratogen.

SUMMARY OF THE INVENTION

Cisplatin analogs of the formula (4,4'-bis[RO]-2,2'-bipyridine)PtCl$_2$ [where, R=—a) (CH$_2$)$_n$CH$_3$, b) —(CH$_2$)$_n$OCH$_3$, or c) —(CH$_2$)$_n$[O(CH$_2$)$_m$]$_y$O(CH$_2$)$_z$CH$_3$ and where n=1, 2, 3, 4, 5, 6, 7, 8, 9 or 10; and m, y and z are independently 0-10] were found to be synthesized by novel chemical synthetic procedures. Analogs of a) where n=2, 3, 4 and 5, and c) where n=2, m=2, y=2, z=1 were found to be unexpectedly more effective in treating numerous cancer cell lines than cisplatin analogs of an identical formula a) where n=1 and 7. The treatments by direct application of the inventive analog and preferably by infusion (intravenous delivery) has been determined to be effective against breast cancer, prostate cancer, lung cancer and melanoma.

BRIEF DESCRIPTION OF THE FIGURES

FIG. 12 is a Table that shows the comparative results of the addition of compounds synthesized according to FIG. 1 at an identical addition concentration for 1 hour on a single cell line.

FIG. 13 is a Table that shows the comparative results of the addition of compounds synthesized according to FIG. 1 at an identical addition concentration for 48 hours on a single cell line.

FIG. 14 is a Table that shows the results of the addition of compounds synthesized according to FIG. 1 where R=—(CH$_2$)$_n$CH$_3$, and n=3.

DETAILED DESCRIPTION OF THE INVENTION

Figure 1:
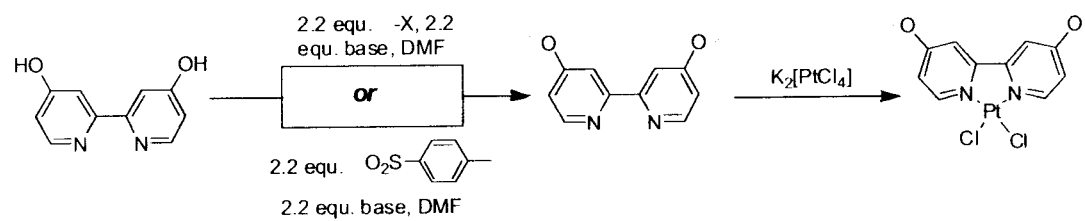
FIG. 1 shows a flow diagram of a novel synthetic process for the manufacture of compounds, including those within the definition of preferred compounds within the scope of the present claims.

A synthetic process manufactures cis-LPtCl$_2$ complex wherein L is a 4,4'-substituted-2,2'-bipyridine compound of 2,2'-bipyridines and having a group R selected from the group consisting of alkoxy groups appended in both the 4,4'-positions of the bipyridine. A first reagent from the group consisting of (4,4'-bis[RO]-2,2'-bipyridine), where, R=—(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$ and where n=1-10; and m, y and z are independently 0-10 is dissolved in a solution with a second reagent of an alkali or alkaline salt of tetrachloro platinum, and the solution is refluxed to produce a precipitate of a (4,4'-bis[RO]-2,2'-bipyridine)PtCl$_2$ where, R=—(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$ and where n=1, . . . 10, and especially where 2, 3, 4 or 5; and m, y and z are independently 0-10. The alkali or alkaline salt of tetrachloro platinum is preferably selected from the group consisting of Na+, K+, and Li+ tetrachloro platinum, although soluble divalent cationic salts may also be used (e.g., Ca$^{+2}$, Mg$^{+2}$, etc.). R is preferably selected (for purposes of ultimate use) from the group consisting of C2-C6 alkyl or alkyl ether. For example, R may be selected from the group consisting of C2-C5 or up to C6 alkyl and an alkali or alkaline salt of tetrachloro platinum comprises potassium tetrachloro platinum.

A method reduces the in vivo viability of cancer cells selected from the group consisting of breast cancer cells, lung cancer cells, prostate cancer cells and melanoma cancer cells. The method includes:

a) identifying a prospective patient having cancer cells selected from the group consisting of breast cancer cells, lung cancer cells, prostate cancer cells and melanoma cancer cells;

b) administering a cisplatinum derivative to the prospective patient so that the cisplatinum derivative will contact the cancer cells; wherein the cisplatin derivative is a 4,4'-bis[RO]-2,2'-bipyridine)PtCl$_2$ where, R is selected from the group consisting of —(CH$_2$)$_n$CH$_3$ where n=2, 3, 4 or 5, and —(CH$_2$)$_n$[O(CH$_2$)$_m$]$_y$O(CH$_2$)$_z$CH$_3$ where n=2, m=2, y=2, z=1.

Although the method has been proven with respect to at least one example each of human (prostate, lung, breast and melanoma) cancer cell lines, there is general acceptance of broad spectrum utility and known effectiveness of cisplatin compounds and derivatives for treating a wide range of human cancer cell lines within the classes of prostate, lung, breast and melanoma human cancer cell lines (such as those typically used in testing procedures for evaluating new treatments, such as within the cell lines selected from the group consisting of:

Lung cancer cells: A549, NCI-H23, NCI-H460, NCI-H522, HOP-62;
Breast cancer cells: MCF7, MDA-MB-231, HCC38, T-47D, MDA-MB-468, SKBR3, ZR75-1;
Prostate cancer cells: DU-145, PC-3, LNCaP; and
Melanoma cancer cells: MDA-MB-435, M14, LOX IMVI, SK-MEL-28).

Because of that general acceptance, and the clear evidence provided herein that the narrow claim of C2-C5 or up to C6 analogs dramatically and unexpectedly outperform both cisplatin and C1 analogs of 4,4'-bis[RO]-2,2'-bipyridine)PtCl$_2$, it is reasonably believed that these present analogs (C2-C5 or up to C6) have unexpected effectiveness in a broader spectrum of human cancer cell lines (within the subgeneric groups of prostate, lung, breast and melanoma human cancer cell lines far beyond both the specific four lines tested), the generally used test lines and the like. This belief is based upon the scientific expectations of the inventors.

It is preferred that the cisplatin derivative consist of a compound within the group consisting of (4,4'-bis[RO]-2,2'-bipyridine)PtCl$_2$ where, R is selected from the group consisting of (CH$_2$)$_n$CH$_3$ where n=2, 3, 4 or 5, and —(CH$_2$)$_n$[O(CH$_2$)$_m$]$_y$O(CH$_2$)$_z$CH$_3$ where n=2, m=2, y=2, z=1.

The present application shows actual performance data for in vivo treatment of at least some human cell lines from the group consisting of human lung cancer cell line A549, human breast cell line T-47D, human melanoma cell line MDA-MB-435 and human prostate cancer cell line DU-415.

Figure 4:
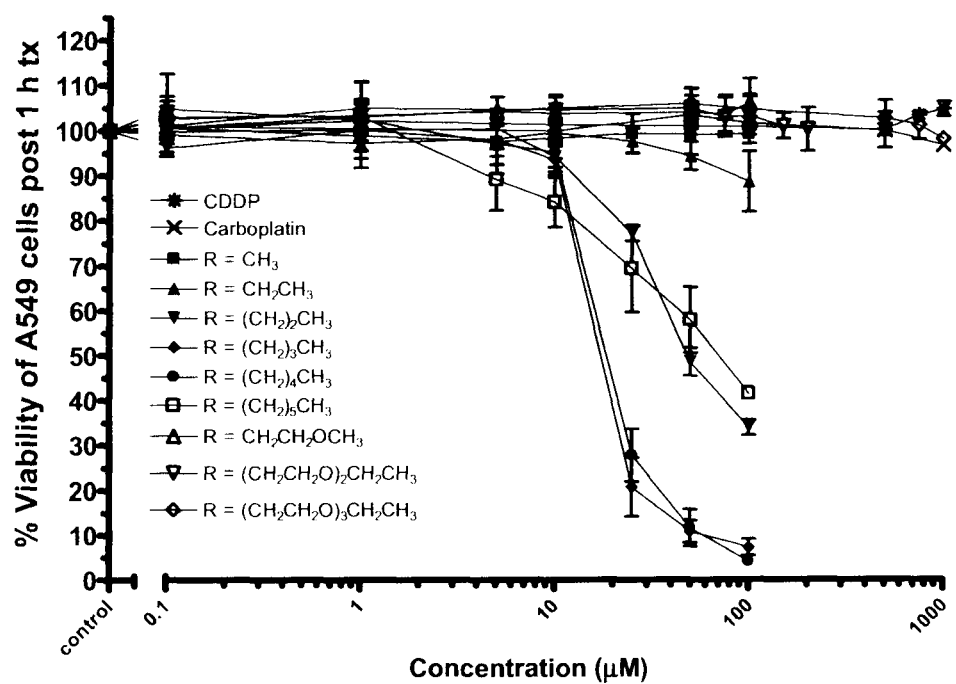
FIG. 4 shows a graphic representation of comparative results of cell viability of a first cancer cell treated for 1 hour at progressive cisplatin and cisplatin derivatives according to the structural formula of FIG. 1.
Figure 5:
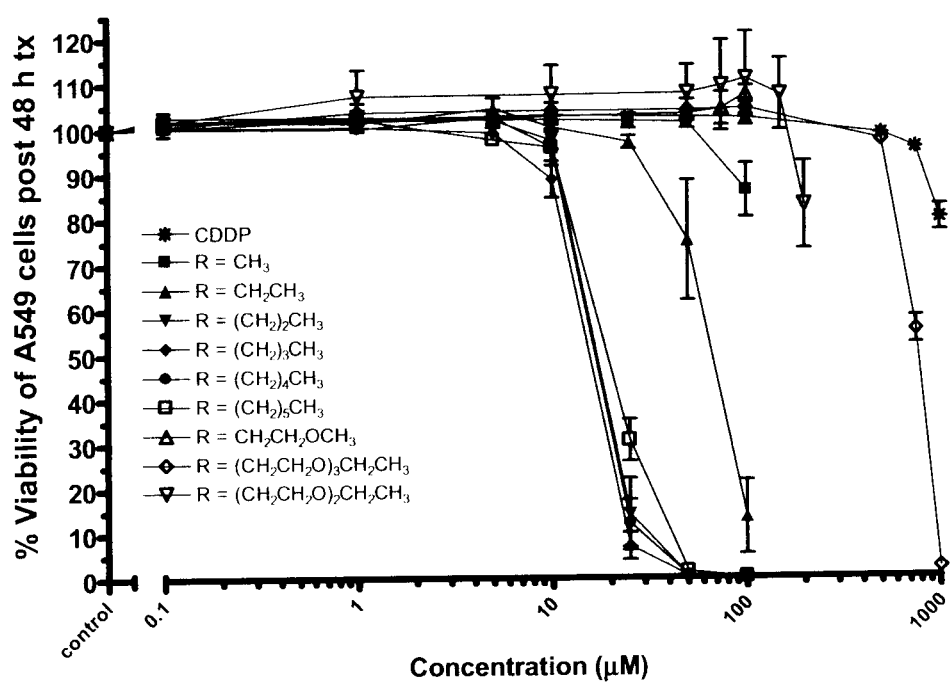
FIG. 5 shows a graphic representation of comparative results of cell viability of a first cancer cell treated for 48 h at progressive cisplatin and cisplatin derivatives according to the structural formula of FIG. 1.

A series of cisplatin analogs of the formula (4,4'-bis[RO]-2,2'-bipyridine)PtCl$_2$ [where, R=—(CH$_2$)$_n$CH$_3$, —(CH$_2$)$_n$OCH$_3$, —(CH$_2$)$_n$[O(CH$_2$)$_m$]$_y$O(CH$_2$)$_z$CH$_3$ (n=1-10; m, y, z=0-10)] were synthesized and characterized using $^1$H NMR, $^{13}$C NMR spectroscopy, and elemental analysis. The antitumor activities of these compounds were examined in a lung cancer cell line (A549) using the MTS cell proliferation assay and the results were compared to that of cisplatin and cisplatin derivatives. Four compounds, where R=—(CH$_2$)$_2$CH$_3$ (EC$_{50}$=48±3 µM), —(CH$_2$)$_3$CH$_3$ (EC$_{50}$=17±1 µM), —(CH$_2$)$_4$CH$_3$ (EC$_{50}$=18±1 µM), —(CH$_2$)$_5$CH$_3$ (EC$_{50}$=66±16 µM), were found to be more effective than CDDP after a one hour treatment; cisplatin had no effect on the A549 cells even up to a 1 mM concentration (FIG. 4 and FIG. 12). Six compounds (R=—CH$_2$CH$_3$ (EC$_{50}$=66±7 µM), —(CH$_2$)$_2$CH$_3$ (EC$_{50}$=17±1 µM), —(CH$_2$)$_3$CH$_3$ (EC$_{50}$=15.4±0.5 µM), —(CH$_2$)$_4$CH$_3$ (EC$_{50}$=16.5±0.5 µM), —(CH$_2$)$_5$CH$_3$ (EC$_{50}$=19.1±0.8 µM), —(CH$_2$CH$_2$O)$_3$CH$_2$CH$_3$ (EC$_{50}$=730±56 µM)) were found to be more effective than CDDP when the treatment time was extended to 48 h (FIG. 5 and FIG. 13). The cytotoxicity of the compound R=—(CH$_2$)$_3$CH$_3$ and cisplatin were also tested on prostate (DU-145, EC$_{50}$=8±2 µM), breast (MCF7, EC$_{50}$=32±5 µM; T-47D, EC$_{50}$=14±2 µM; HCC38, EC$_{50}$=5±1 µM), and melanoma (MDA-MB-435, EC$_{50}$=3.3±0.4 µM) cancer cell lines. Cisplatin had little or no effect on the cell lines tested even up to a 1 mM concentration. These results indicate the potential of these compounds to be used as effective chemotherapeutic drugs.

The current invention provides new platinum complexes that have the potential to replace current platinum-containing drugs used in clinical treatment of cancer. These compounds of the present invention exhibit unexpectedly improved performance in addressing the viability of cancer cells as compared to cisplatin and analogs of cisplatin compounds within the scope of the invention. A novel method of synthesizing the compounds of the invention and analogs of those compounds simplifies the synthetic process.

Figure 3:
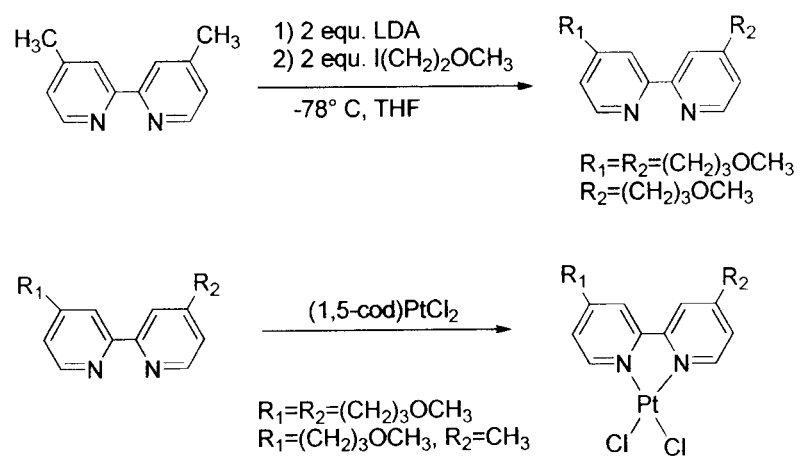
FIG. 3 shows two different synthetic processes that may be used that combined are a novel synthetic process for manufacturing prior art cisplatin compounds.

As depicted in the synthetic scheme of FIG. 1 and FIG. 3, the compounds described are composed of alkoxy-substituted 2,2'-bipyridine or alkyl-substituted 2,2'-bipyridine (respectively) coordinated to a platinum center; these complexes are novel and have not been previously reported. The platinum compound with R=CH$_2$CH$_3$ was synthesized previously by an alternative procedure, but no literature on activity against cancer cells has been reported. The synthesis of these complexes as described herein is a direct two-step procedure that generally gives high yields. The starting compound used for the novel synthesis of the ligands is [2,2'-bipyridine]-4,4'-diol, which can be deprotonated by a mild base such as K$_2$CO$_3$ or Cs$_2$CO$_3$, thus obviating the need for a strong base such as LDA.

Several of the complexes synthesized have been tested in an experimental setting of human cancer cell line non-responsiveness to cisplatin. We find these novel Pt-containing compounds exceptionally effective at selectively inducing cancer cell death whereas cisplatin is essentially without significant effect in this experimental setting.

For most human tumors the limit of clinical or radiologic detection is about 1 gram of tissue containing approximately 10$^9$ cells. Surgical biopsies may lower the limit of detection to a point not less than 1 tumor cell in 1,000 normal tissue cells. The human cancer cell lines in this invention are initially cultured at 2,100 cells in a volume of 100 µl of medium. At the time of treatment, the cancer cell lines are approximately 8,000 cells in 100 µl of culture medium. The EC$_{50}$ of the platinum compound with R=(CH$_2$)$_3$CH$_3$ for the A549 cell line is 0.014 µg/µl. Therefore, as little as 1.4 µg of the novel platinum compound effectively killed 50% of 8,000 tumor cells in a setting wherein the clinically approved platinum compounds were completely ineffective. Administered intravenously, the clinical dosage of cisplatin (PLATINOL) ranges from 20 to 600 mg/m$^2$. Carboplatin (PARAPLATIN) clinical doses range from 300-360 mg/m$^2$ and for oxaliplatin (ELOXATIN) clinical doses range from 65-85 mg/m$^2$. Given the lack of effects of cisplatin, carboplatin, and oxaliplatin in this experimental setting, the new platinum complexes described herein may require substantially reduced doses in a clinical setting.

Clinical Methods

MTS Assay

Cells were cultured at a density of 2.1×10$^3$ cells per well in flat bottomed 96-well plates in 100 µl of medium supplemented with 10% fetal bovine serum (FBS), 25 mM HEPES buffer (pH 7.4), Penicillin (100 U/ml) and Streptomycin (100 µg/ml) and incubated at 37° C. in a humidified, 5% CO$_2$ atmosphere for 2 days. The cells were then treated with DMSO or the appropriate drugs for 1 hour, washed thrice with 100 µl phosphate buffered saline (PBS), and incubated in 100 µl of fresh medium. After 2 days, the medium was replace with 120 µl of medium containing 50 µM phenazine ethosulfate (PES) and 317 µg/mL CellTiter 96® Aq$_{ueous}$ One Solution Reagent (MTS) (Promega, Madison, Wis.). After 4 hours in culture the cell viability was determined by measuring the absorbance at 490 nm using a Tecan Infinite M1000 plate reader.

Synthesis of Ligand

The alkylhalide or alkyl tosylate containing the desired alkyl group (2.2 equiv.) was added to a mixture of 2,2'-bipyridine-4,4'-diol (1 equiv.) and $K_2CO_3$ or $Cs_2CO_3$ (2.2 equiv.) in DMF at ~60° C. The suspension was heated to reflux for 48 h then allowed to cool to ambient temperature. The salt was removed by vacuum filtration and washed with dimethylformamide (DMF). Rotary evaporator was used to remove the solvent from the filtrate. The solid residue was washed with water and collected by vacuum filtration. In most cases, recrystallization in the appropriate solvent revealed the pure product as shiny, white crystals.

Synthesis of Pt Complexes

According to the flow schemes in FIG. 1, $K_2PtCl_4$ (tetrachloro platinum 1.2 equiv.) was dissolved in 1-2 mL of $H_2O$ and added to a solution of 4,4'-bisalkoxy-2,2'-bipyridine (1 equiv.) in acetone. The mixture was refluxed for 24 hours. Yellow solid precipitated out either in refluxing condition or upon cooling. Water was added to ensure complete precipitation of the product. The crude product was separated by vacuum filtration. The pure product was obtained by recrystallization or washing with the appropriate solvent.

Figure Legends

FIG. 1. Synthetic scheme for the synthesis of platinum complexes. Where $R=(CH_2)_nCH_3$, $(CH_2)_nOC_3$, $(CH_2)_n[O(CH_2)_m]_yO(CH_2)_zCH_3$ (n=1-10; m, y, z=0-10) and X=Br, Cl, I. In this process, 4,4'-bishydroxy-2,2'-bipyridine is dissolved in an organic solvent (e.g., basic dimethylformamide) and is alkylated (R=alkyl) with at least 2 equivalents of an alkyl halide (e.g., R—X, wherein R=alkyl and X is a halide, especially, in order of preference, Cl, Br, I and F) or alkyl tosylate. The resulting of 4,4'-bisalkoxy-2,2'-bipyridine is then converted to the platinum compounds of the invention by reaction (e.g., under reflux) with a soluble salt (e.g., $A_2[PtCl_4]$, wherein A is a monovalent cation, such as Na+, K+, Li+ and the like). The precipitate is filtered and washed.

Figure 2A:
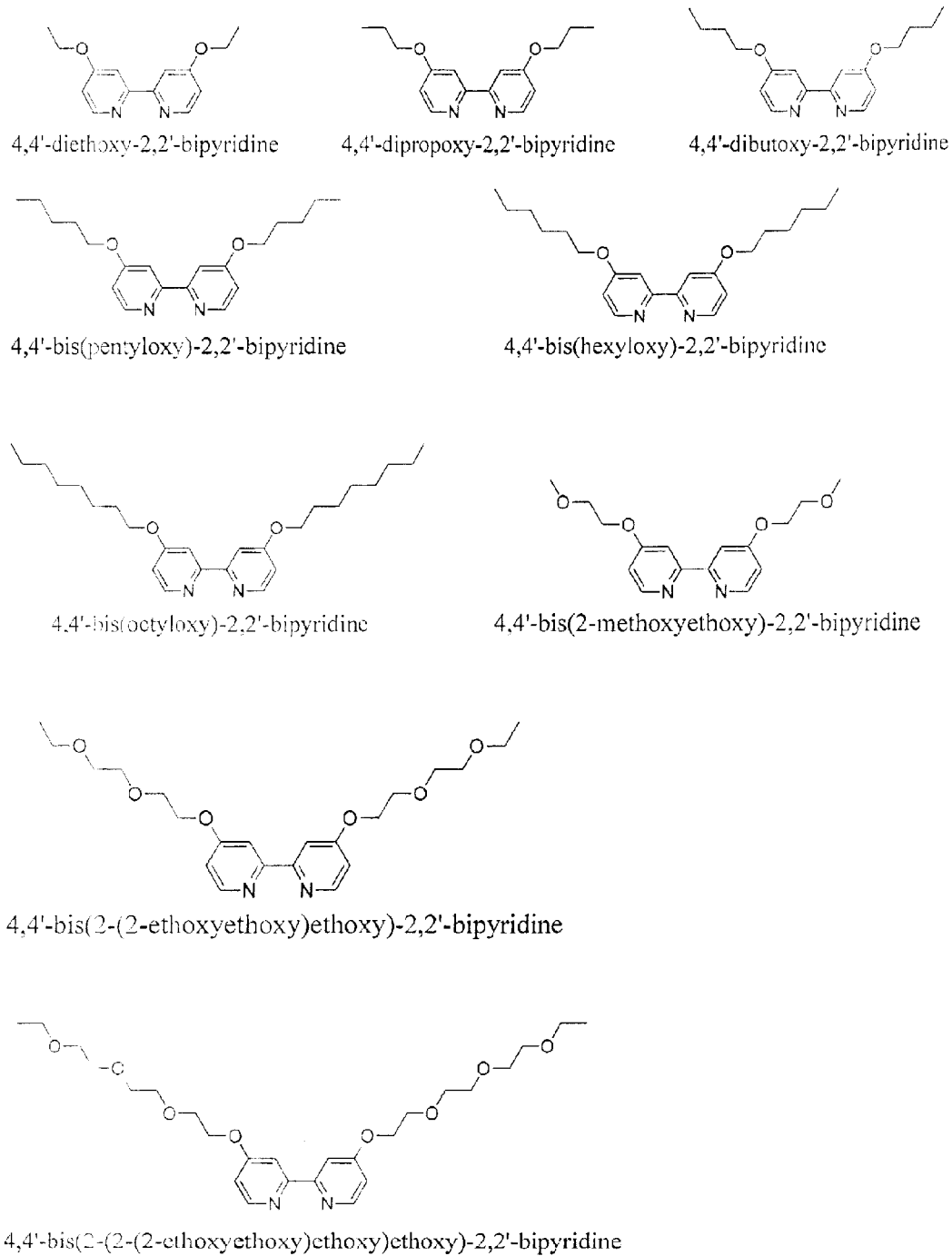
FIG. 2 shows a series of chemical structures of compounds within the scope of those synthesized according to the definition of FIG. 1 with m, n, y and z as defined herein.
Figure 2B:
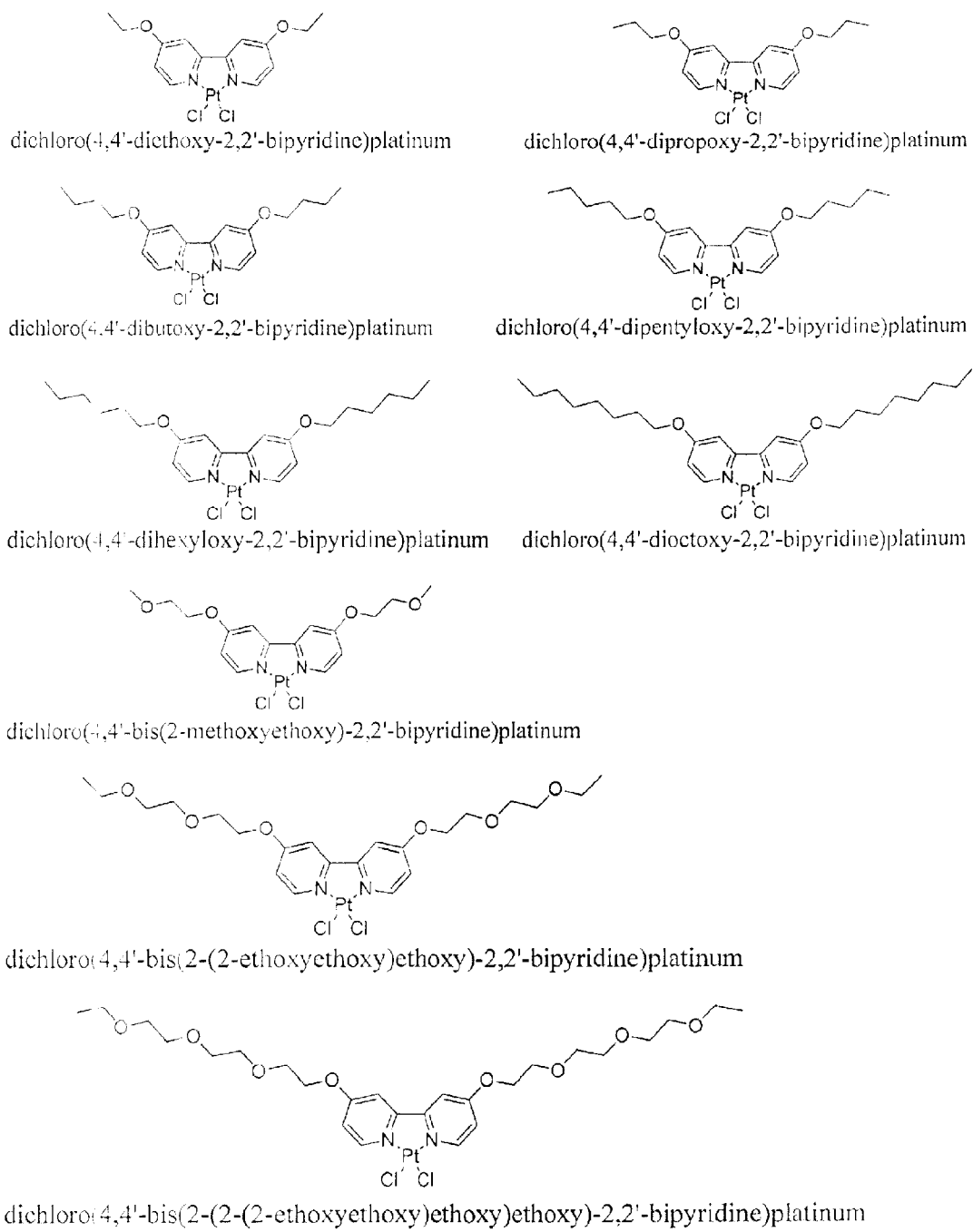

FIG. 2 is a list of some structures of synthesized compounds.

FIG. 3 shows the synthetic scheme from Published U.S. patent application Ser. No. 11/400,886.

FIG. 4 shows the graphic representation of cytotoxic activity of the synthesized complexes vs. CDDP and carboplatin against A549 human lung cancer cells. Cells were treated with CDDP or the platinum analogs at various concentrations for 1 hour and the viability was determined 48 h post-treatment using the MTS assay.

FIG. 5 shows the graphic representation of cytotoxic activity of the synthesized complexes vs. CDDP and carboplatin against A549 human lung cancer cells. Cells were treated with CDDP or the platinum analogs at various concentrations for 48 hour and the viability was determined post-treatment using the MTS assay.

Figure 6:
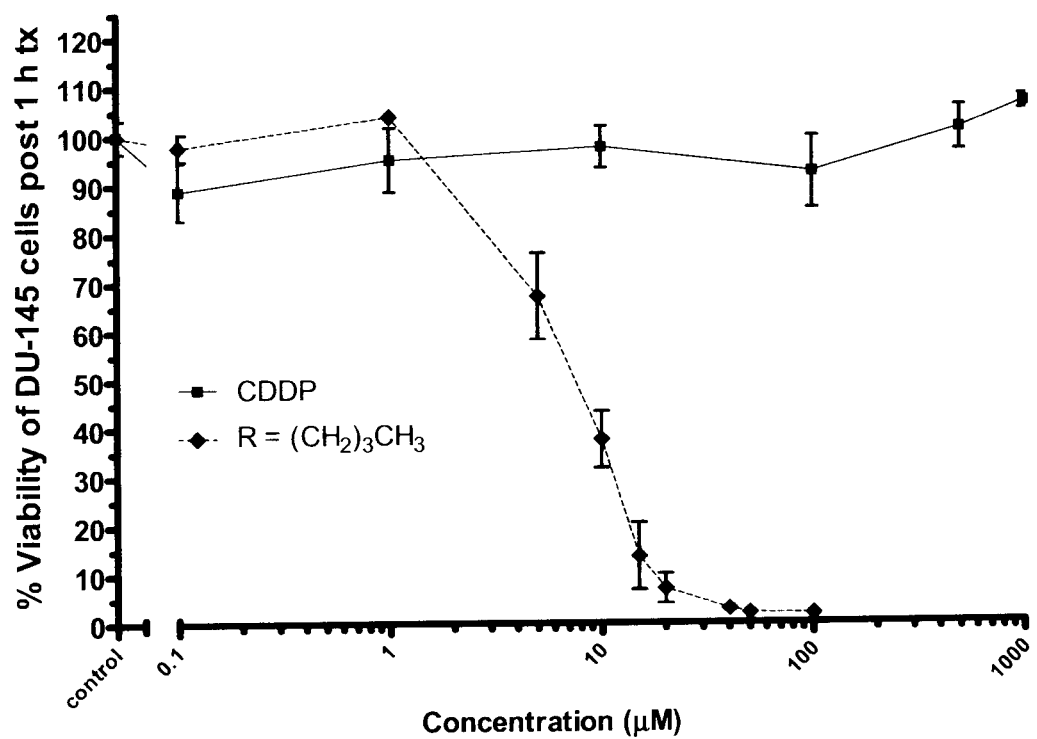
FIG. 6 shows a graphic representation of comparative results of a second cancer cell viability between cisplatin and one cisplatin derivative at progressive concentrations.

FIG. 6 shows the graphic representation of the cytotoxic activity of the synthesized complexes vs. CDDP against DU-145 human prostate cancer cells. Cells were treated with CDDP or the platinum analog at various concentrations for 1 hour and the viability was determined 48 h post-treatment using the MTS assay.

Figure 7:
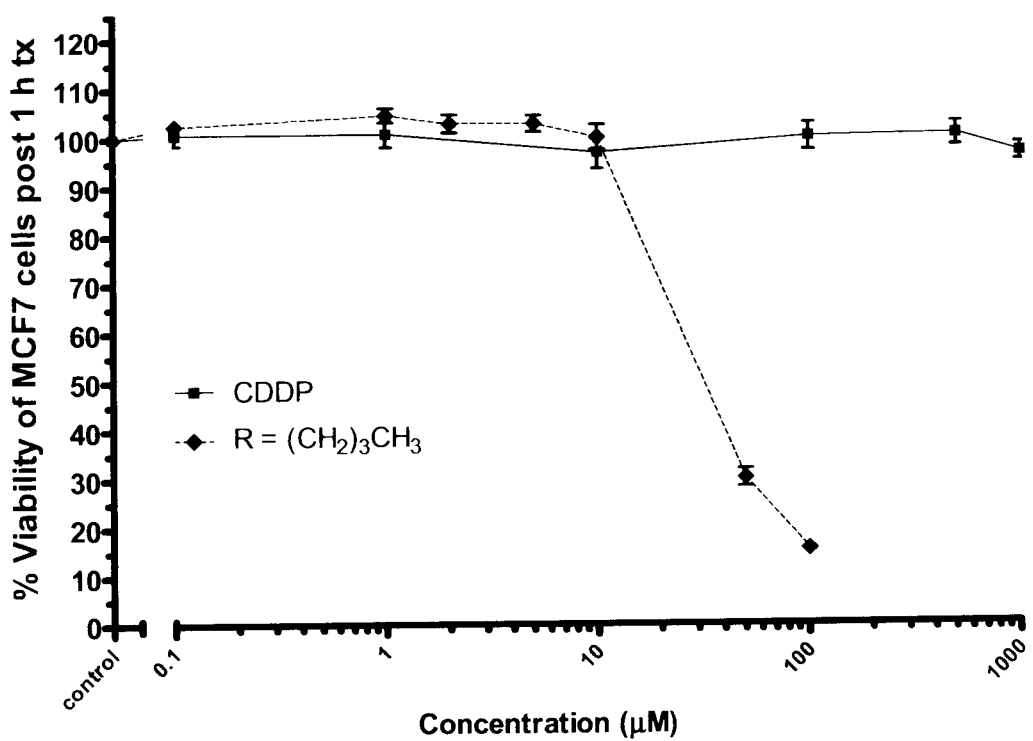
FIG. 7 shows a graphic representation of comparative results of a third cancer cell viability between cisplatin and one cisplatin derivative at progressive concentrations.

FIG. 7 shows the graphic representation of the cytotoxic activity of the synthesized complexes vs. CDDP against MCF7 human breast cancer cells. Cells were treated with CDDP or the platinum analog at various concentrations for 1 hour and the viability was determined 48 h post-treatment using the MTS assay.

Figure 8:
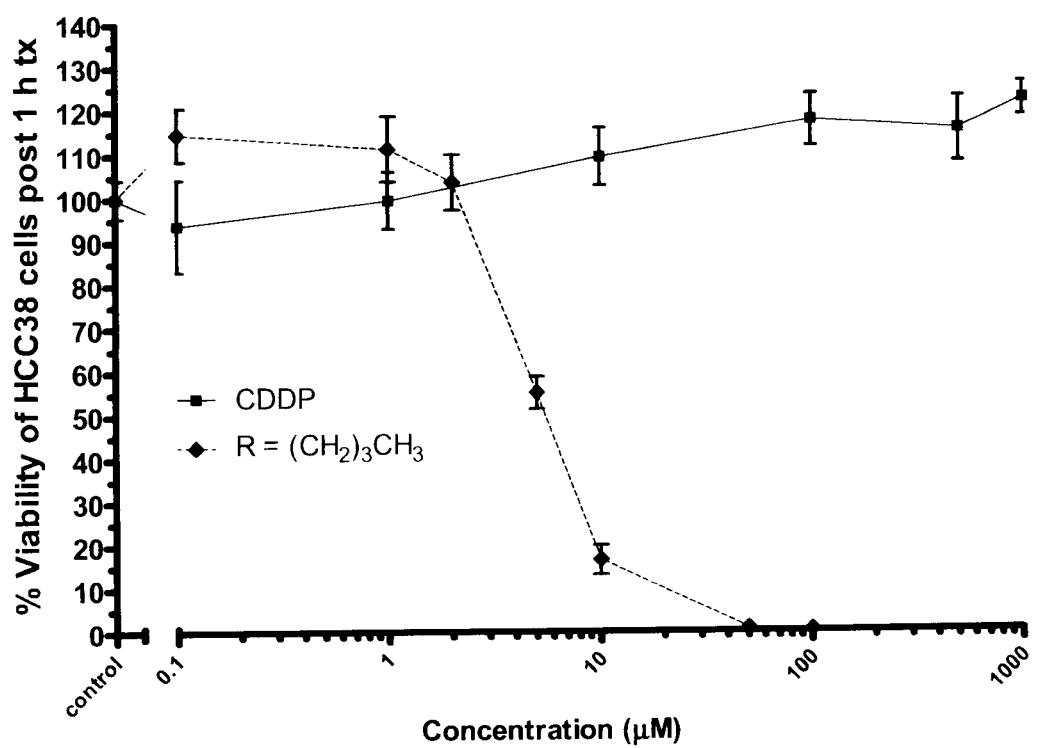
FIG. 8 shows a graphic representation of comparative results of a fourth cancer cell viability between cisplatin and one cisplatin derivative at progressive concentrations.

FIG. 8 shows the graphic representation of the cytotoxic activity of the synthesized complexes vs. CDDP against HCC38 human breast cancer cells. Cells were treated with CDDP or the platinum analog at various concentrations for 1 hour and the viability was determined 48 h post-treatment using the MTS assay.

Figure 9:
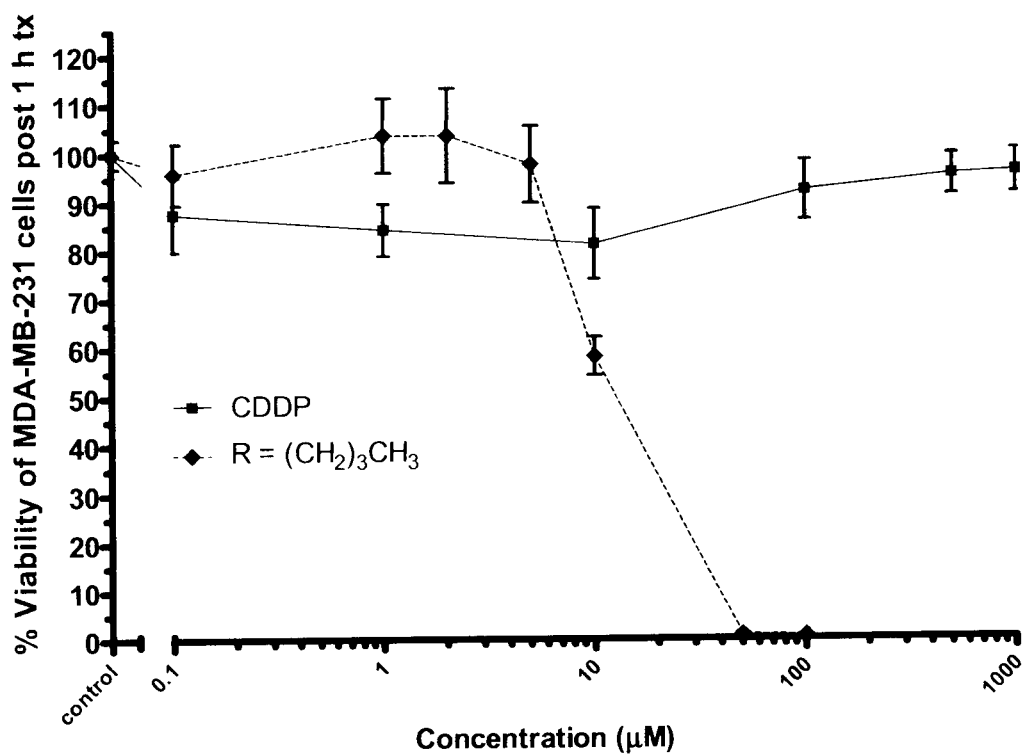
FIG. 9 shows a graphic representation of comparative results of a fifth cancer cell viability between cisplatin and one cisplatin derivative at progressive concentrations.

FIG. 9 shows the graphic representation of the cytotoxic activity of the synthesized complexes vs. CDDP against MDA-MB-231 human breast cancer cells. Cells were treated with CDDP or the platinum analog at various concentrations for 1 hour and the viability was determined 48 hours post-treatment using the MTS assay.

Figure 10:
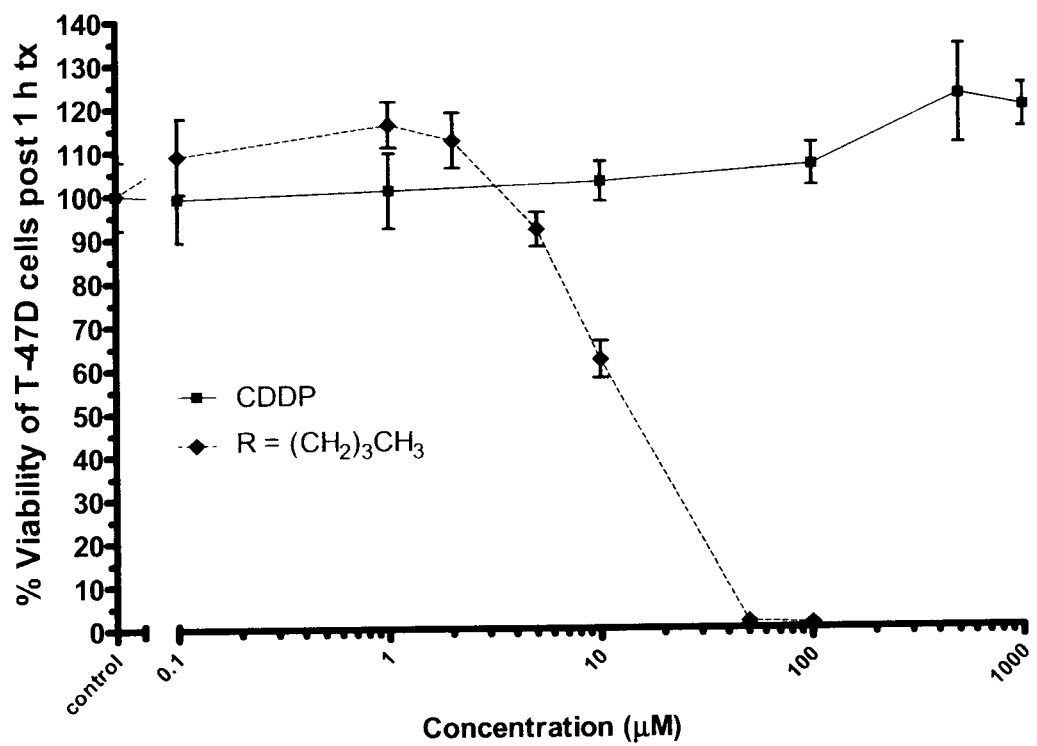
FIG. 10 shows a graphic representation of comparative results of a sixth cancer cell viability between cisplatin and one cisplatin derivative at progressive concentrations.

FIG. 10 shows the graphic representation of the cytotoxic activity of the synthesized complexes vs. CDDP against T-47D human breast cancer cells. Cells were treated with CDDP or the platinum analog at various concentrations for 1 hour and the viability was determined 48 h post-treatment using the MTS assay.

Figure 11:
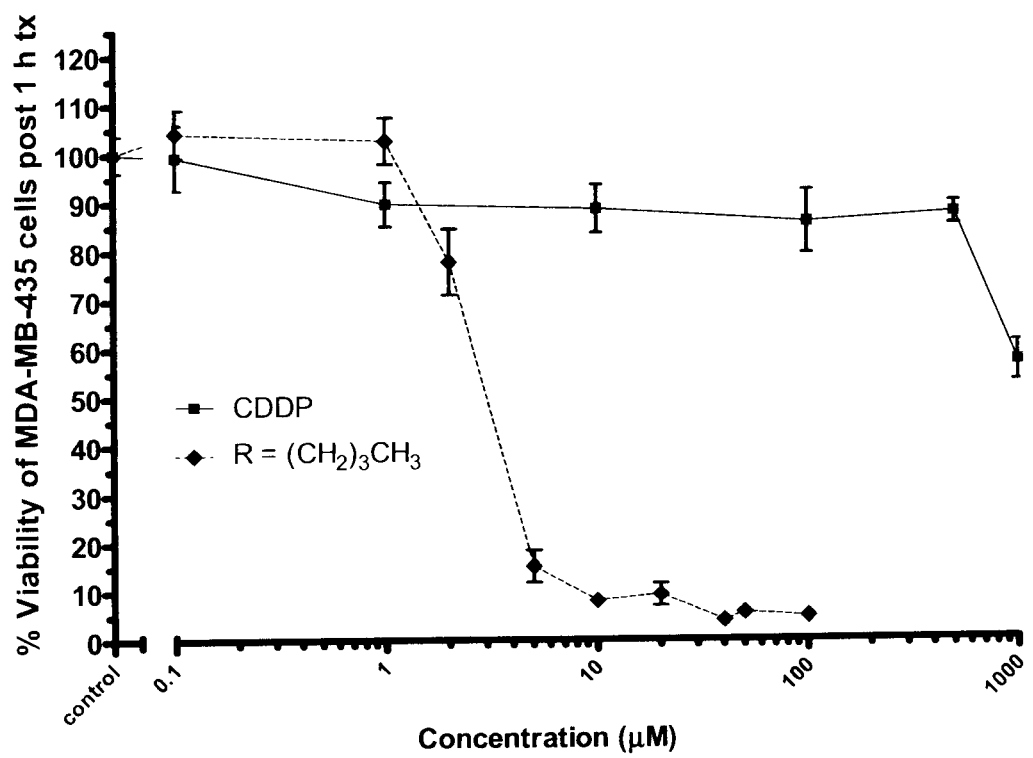
FIG. 11 shows a graphic representation of comparative results of a seventh cancer cell viability between cisplatin and one cisplatin derivative at progressive concentrations.

FIG. 11 shows the graphic representation of the cytotoxic activity of the synthesized complexes vs. CDDP against MDA-MB-435 human melanoma cancer cells. Cells were treated with CDDP or the platinum analog at various concentrations for 1 hour and the viability was determined 48 h post-treatment using the MTS assay.

FIG. 12 shows Table 1. This is a table comparison of effective concentrations that gives 50% cell death ($EC_{50}$) determined from A549 MTS assay data for the 1 h treatment.

FIG. 13 shows Table 2. This is a table comparison of effective concentrations that gives 50% cell death ($EC_{50}$) determined from A549 MTS assay data for the 48 h treatment.

FIG. 14 shows Table 3. This is a table comparison of $EC_{50}$ (μM) determined from MTS assay data of the various cell lines treated with CDDP or the analog where $R=(CH_2)_3CH_3$. Commonly Used Cancer Cell Lines Expected to Provide Evidence of the Effectiveness of the Compounds of the Present Invention Lung: A549, NCI-H23, NCI-H460, NCI-H522, HOP-62
Breast: MCF7, MDA-MB-231, HCC38, T-47D, MDA-MB-468, SKBR3, ZR75-1
Prostate: DU-145, PC-3, LNCaP
Melanoma: MDA-MB-435, M14, LOX IMVI, SK-MEL-28

Academic literature for related derivatives exists (1997-present) supporting the observation of route functionality later presented herein. These related derivatives have three or four methylene "spacers" between the bipyridine ring and a fluorocarbon tail of 6-10 carbons in length. U.S. Pat. No. 6,875,886 (Frangioni) describes reagents and methods for diagnosis, detection and treatment of cancers (for example, prostate cancers). In particular, the invention provides methods to generate various functionalized (prostate-specific membrane antigen (PSMA)) ligands, and their uses in diagnosis, detection, imaging, and treatment of prostate cancers, especially those overexpressing PSMA.

This disclosure encompasses inventions including the syntheses of a group of new cisplatin analogs, and the use of these cisplatin analogs to treat cancer. Generically, the present technology includes a cisplatin complex and a method of treating a patient having cancerous cells affecting tissue comprising providing the cis-$LPtCl_2$ complex wherein L is a 4,4'-substituted-2,2'-bipyridine or a compound comprising 2,2'-bipyridines having the defined groups R appended in the 4,4' positions of the 2,2'-bipyridine to the affected tissue. This is preferably done without encapsulation or carriage of the complex in a lipid or liposome, but effected in a suspended or dissolved format without fatty carriers. The concentration of the complexes administered locally may be effective in picogram quantities at the site (e.g., at least 1.0 picograms per square mm of cancerous cell environment or about 20 to 100 mg/m² for 6 to 8 hours, the environment being the entire volume region where cells have been identified and the in vivo blood supply of the patient to be treated and not the volume of cancerous cells themselves. Higher concentrations and amounts of the complex are likely to be administered, especially with general administration, with nanogram concentrations (e.g., 1.0 nanograms per 1.0 mm cancerous cell environment) and even milligram concentrations (e.g., 1.0 milligram per 1.0 mm cancerous cell environment). This amount is greatly increased over time (e.g., these amounts may be delivered over 10 seconds, thirty seconds, minutes, hours or days), as the treatments are not single events but either episodic or continuous provision techniques. The providing of the complex to the affected tissue may be performed by at least one of general administration (e.g., oral, intravenous, topical, transdermal, etc.) of the complex and affected tissue targeted administration of the complex (e.g., diffusion from a catheter, implantation, perfusion through a catheter, injection, infusion and the like). The complex may have L comprising a 4,4'-substituted 2,2'-bipyridine. The complex may have the 4 and 4' substituents symmetrical or asymmetrical with respect to each other.

The complexes of the present invention may also be represented by the formula cis-LPtCl$_2$ where L is a 4,4'-substituted-2,2'-bipyridine The substituents may be those groups defined herein as R, wherein R=—(CH$_2$)$_n$CH$_3$, —(CH$_2$)$_n$OCH$_3$, —(CH$_2$)$_n$[O(CH$_2$)$_m$]$_y$O(CH$_2$)$_z$CH$_3$ (n=1-10; m, y, z=0-10.

This class of cisplatin analogs maintains the original active sites of cisplatin (i.e., two Pt—Cl bonds in cis position). In addition, there are appended alkyl chain to assist in binding to the major and minor grove of DNA. The complex of the present invention may be used to treat cancer tissue. Data are supplied describing potential utility in treatment of various cancer cell lines including breast cancer, prostate cancer, lung cancer and melanoma. In particular in-vitro experiments compare cancer cell survival comparative trials for the complex where within the scope of R=a) —(CH$_2$)$_n$CH$_3$ (n=1-5 or b) —(CH$_2$)$_n$[O(CH$_2$)$_m$]$_y$O(CH$_2$)$_z$CH$_3$ (n=2, m=2, y=0-2, z=0-1, in a) R=propyl and the structural core nucleus is cis-Platin.

These cisplatin analogs will bind DNA with secondary intermolecular interactions (Hydrogen Bonding or electrostatic effects). Replacement of the amine ligands (NH$_3$) with functionalized imine ligands (2,2'-bipyridine) affords the opportunity to retain the Pt binding site (for Guanine and Cytosine) and implement new group extensions for interaction with the double helix groove wall (major and minor groves).

The scheme shown in FIG. 1 exhibits a method for synthesizing all of the derivatives prepared to date and those of the formula in FIG. 1 and shown in FIG. 2. They have been characterized by NMR spectroscopy and/or with satisfactory elemental analysis.

As noted elsewhere, all of the compounds described in the practice of this technology, including alkyl groups with ether linkages may be synthesized by the selection of the appropriate reagent. Providing multiple and otherwise identical reaction paths would be superfluous for all of the alternatives.

For the formula (4,4'-bis[RO]-2,2'-bipyridine)PtCl$_2$ where, R=—(CH$_2$)$_n$OCH$_3$ a compound has been made where R=(CH$_2$)$_2$OCH$_3$, which is within the scope of this disclosure where R=—(CH$_2$)$_n$OCH$_3$ with n=2, 3 or 4 (or even 5) for treatment application.

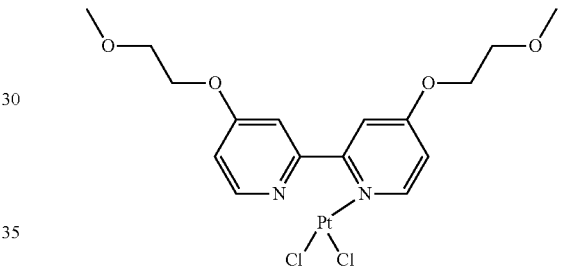

dichloro(4,4'-bis(2-methoxyethoxy)-2,2'-bipyridine)platinum

For the formula (4,4'-bis[RO]-2,2'-bipyridine)PtCl$_2$ where, R=—(CH$_2$)$_n$[O(CH$_2$)$_m$]$_y$O(CH$_2$)$_z$CH$_3$ and n=1-10; m, y, z=0-10.

At least three compounds synthesized fit into this formulation (see below):

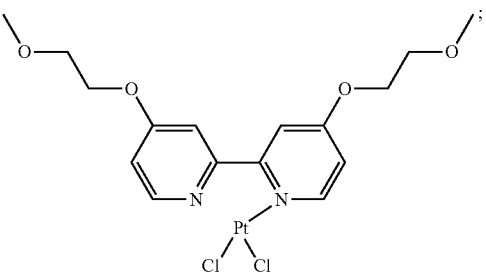

dichloro(4,4'-bis(2-methoxyethoxy)-2,2'-bipyridine)platinum

R = —(CH$_2$)$_2$[O(CH$_2$)$_0$]$_0$O(CH$_2$)$_0$CH$_3$

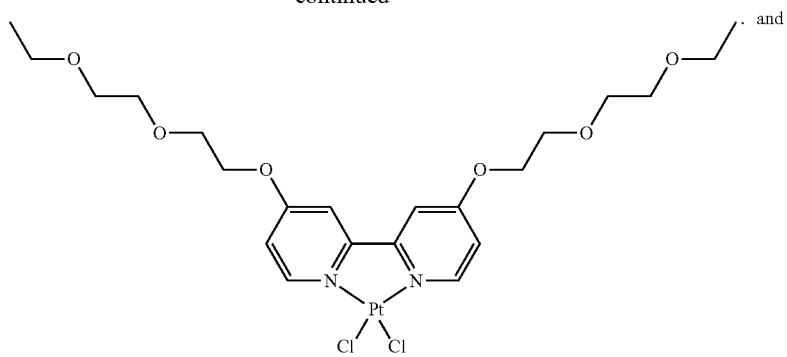

dichloro(4,4'-bis(2-(2-ethoxyethoxy)ethoxy)-2,2'-bipyridine)platinum

R = —(CH$_2$)$_2$[O(CH$_2$)$_2$]$_1$O(CH$_2$)$_1$CH$_3$

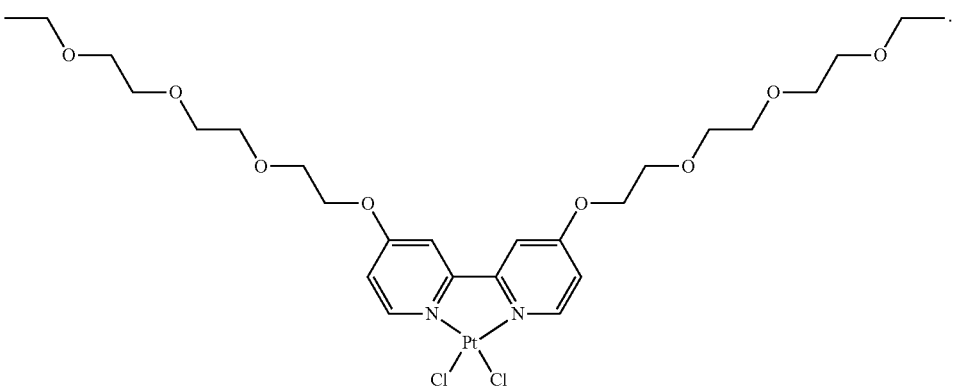

dichloro(4,4'-bis(2-(2-(2-ethoxyethoxy)ethoxy)ethoxy)-2,2'-bipyridine)platinum

R = —(CH$_2$)$_2$[O(CH$_2$)$_2$]$_2$O(CH$_2$)$_1$CH$_3$

These compounds were tested using the A549 lung cancer cell line (see FIGS. 4 and 5)

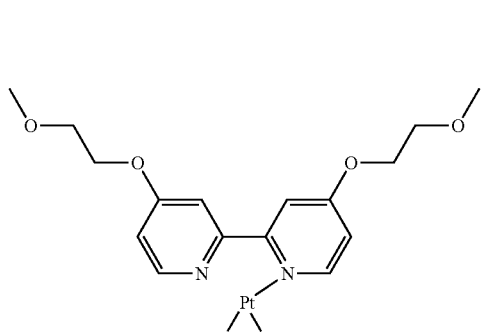

dichloro(4,4'-bis(2-methoxyethoxy)-2,2'-bipyridine)platinum

R = —(CH$_2$)$_2$[O(CH$_2$)$_0$]$_0$O(CH$_2$)$_0$CH$_3$

The compound shown above could only be tested up to a concentration of 100 μM because of solubility. It was not effective for 1 or 48 h treatment.

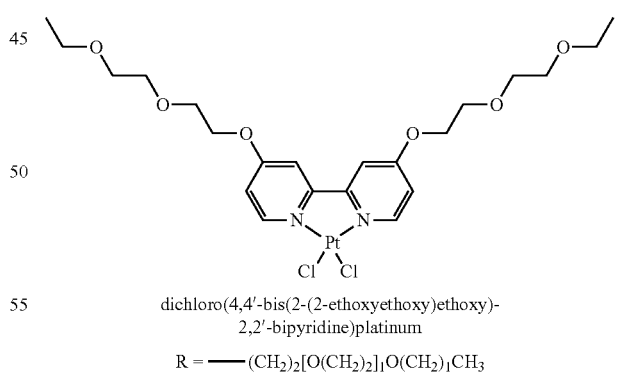

dichloro(4,4'-bis(2-(2-ethoxyethoxy)ethoxy)-2,2'-bipyridine)platinum

R = —(CH$_2$)$_2$[O(CH$_2$)$_2$]$_1$O(CH$_2$)$_1$CH$_3$

The compound shown above could only be tested up to a concentration of 200 μM because of solubility. It was not effective for 1 h treatment, but was slightly effective for 48 h treatment at 200 μM. This still might be useful in treatments as slow acting effects on cancer cells might also be less toxic to normal cells, providing useful, if less dramatic, results in treatment.

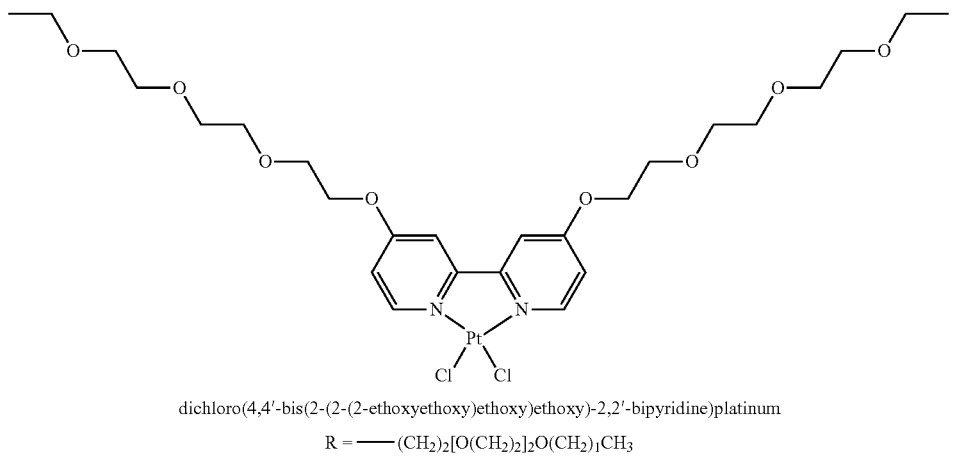

dichloro(4,4'-bis(2-(2-(2-ethoxyethoxy)ethoxy)ethoxy)-2,2'-bipyridine)platinum

R = —(CH$_2$)$_2$[O(CH$_2$)$_2$]$_2$O(CH$_2$)$_1$CH$_3$

20

The compound shown above has some water solubility (a 5 mM solution in water can be made). Stock solution was dissolved in DMSO and was tested up to a concentration of 1000 μM (in 2% DMSO). It was not effective for 1 h treatment, but was effective for 48 h treatment at concentrations higher than 500 μM (cisplatin is not very effective at these conditions). This last compound should be protected for treatment application due to its water solubility and effectiveness at longer exposure time. Thus, the scope of the claimed subject matter for treatment of cancer cells in a live patients includes

R=—(CH$_2$)$_2$[O(CH$_2$)$_2$]$_2$O(CH$_2$)$_1$CH$_3$.

The term "treatment" used in the method claims and disclosure herein is a term well understood in the field of medical technology. It is not equivalent to a cure, but it is a procedure with identifiable beneficial effects in reducing numbers or concentrations of cancer cells and/or slowing the growth of cancer cells without immediate impact on the viability of the patient. That is, a treatment is a process by which at least some measurable beneficial effects on addressing the presence of cancer cells is a result of the use of that process, alone or in combination with other treatments, chemistry or procedures. To be more emphatic, it must be understood in the field of oncology being described herein that the word "treatment" does not mean cure, as would be regarded by lay persons. Rather, treatment is part of a regimen or procedure or therapy that can slow cancer cell growth, reduce cancer cell growth, stop cancer cell growth, limit the reproducibility of cancer cells, cause deterioration in cancer cells, increase mortality of cancer cells, and the like, any of which has potential benefits over the absence of treatment. The process of treatment therefore does not absolutely imply or require a result that a lay person would regard as a cure.

As defined in the claims, several derivatives and their process of manufacture should be protected as novel intellectual property. As support for this assertion, the C2-C5 or up to C6 derivatives have been isolated, platinum complexes generated, and cytotoxicity determined in several cell lines. The di-substituted derivatives have been studied extensively as the elemental analysis, $^1$H NMR and $^{13}$C NMR, and have been acquired for ligands. The platinum complex has been treated in similar fashion. In all cases the analyses support the composition of the ligand and complex and are of publication quality.

What is claimed:

1. A synthetic process for manufacturing cis-LPtCl$_2$ complex wherein L is a 4,4'-substituted-2,2'-bipyridine compound comprising 2,2'-bipyridines having a group R selected from the group consisting of alkoxy groups appended in both the 4,4'-positions of the bipyridine, wherein a first reagent selected from the group consisting of 4,4'-bis[RO]-2,2'-bipyridine, where, R=—(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$ and where n=1, 2, 3, 4, 5, 6, 7, 8, 9 or 10; and m, y and z are independently 0-10 is dissolved in a solution with a second reagent comprising an alkali or alkaline salt of tetrachloro platinum, and the solution is refluxed to produce a precipitate comprising (4,4'-bis[RO]-2,2'-bipyridine)PtCl$_2$ where, R=—(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$ and where n=2, 3, 4 or 5 and m, y and z are independently 0-10.

2. The synthetic process of claim 1 wherein the alkali or alkaline salt of tetrachloro platinum is selected from the group consisting of Na+, K+, and Li+ tetrachloro platinum.

3. The synthetic process of claim 2 wherein R is selected from the group consisting of C2-C6 alkyl.

4. The synthetic process of claim 3 wherein R is selected from the group consisting of C2-C6alkyl and an alkali or alkaline salt of tetrachloro platinum comprises potassium tetrachloro platinum.

5. A method of reducing the in vivo viability of cancer cells selected from the group consisting of breast cancer cells, lung cancer cells, prostate cancer cells and melanoma cancer cells comprising:
   a) identifying a prospective patient having cancer cells selected from the group consisting of breast cancer cells, lung cancer cells, prostate cancer cells and melanoma cancer cells;
   b) administering a cisplatin derivative to the prospective patient so that the cisplatinum derivative will contact the cancer cells;
   wherein the cisplatin derivative is a (4,4'-bis[RO]-2,2'-bipyridine)PtCl$_2$ where, R is selected from the group consisting of —(CH$_2$)$_n$CH3 where n=2, 3, 4 or 5, and —(CH$_2$)$_n$[O(CH$_2$)$_m$]$_y$O(CH$_2$)$_z$CH$_3$ where n=2, m=2, y=2, z=1.

6. The method of claim 5 wherein the cancer cells have been identified as having at least some cancer cells within the cell lines selected from the group consisting of:
   Lung cancer cells: A549, NCI-H23, NCI-H460, NCI-H522, HOP-62;

Breast cancer cells: MCF7, MDA-MB-231, HCC38, T-47D, MDA-MB-468, SKBR3, ZR75-1;

Prostate cancer cells: DU-145, PC-3, LNCaP; and

Melanoma cancer cells: MDA-MB-435, M14, LOX IMVI, SK-MEL-28.

7. The process of claim 1 wherein the cisplatin derivative consist of a compound within the group consisting of (4,4'-bis[RO]-2,2'-bipyridine)PtCl$_2$ where, R is selected from the group consisting of —(CH$_2$)$_n$CH$_3$, where n=2, 3, 4 or 5.

8. The method of claim 6 wherein the cisplatin derivative consist of a compound within the group consisting of (4,4'-bis[RO]-2,2'-bipyridine)PtCl$_2$ where, R is selected from the group consisting of —(CH$_2$)$_n$CH$_3$, where n=2, 3, 4 or 5.

9. The process of claim 1 wherein the cisplatin derivative consist of a compound within the group consisting of (4,4'-bis[RO]-2,2'-bipyridine)PtCl$_2$ where, R is selected from the group consisting of —(CH$_2$)$_n$[O(CH$_2$)$_m$]$_y$O(CH$_2$)$_z$CH$_3$ where n=2, m=2, y=2, z=1.

10. The method of claim 6 wherein the cisplatin derivative consist of a compound within the group consisting of (4,4'-bis[RO]-2,2'-bipyridine)PtCl$_2$ where, R is selected from the group consisting of —(CH$_2$)$_n$[O(CH$_2$)$_m$]$_y$O(CH$_2$)$_z$CH$_3$ where n=2, m=2, y=2, z=1 where n=2, 3 or 4.

11. The method of claim 6 wherein the cancer cells have been identified as having at least some cancer cell lines selected from the group consisting of human lung cancer cell line A549.

12. The method of claim 6 wherein the cancer cells have been identified as having at least some cancer cell lines selected from the group consisting of human breast cell line T-47D.

13. The method of claim 6 wherein the cancer cells have been identified as having at least some cancer cell lines selected from the group consisting of human melanoma cell line MDA-MB-435.

14. The method of claim 6 wherein the cancer cells have been identified as having at least some cancer cell lines selected from the group consisting of human prostate cancer cell line DU-415.

15. The method of claim 5 wherein the cisplatin compound is selected from the a compound with the group consisting of:
(4,4'-bis[RO]-2,2'-bipyridine)PtCl$_2$,
where R=—(CH$_2$)$_n$OCH$_3$ with n=2, 3, 4 or 5.

16. The method of claim 6 wherein the cisplatin compound is selected from a compound with the group consisting of:
(4,4'-bis[RO]-2,2'-bipyridine)PtCl$_2$,
where R=—(CH$_2$)$_n$OCH$_3$ with n=2, 3 or 4.

17. The method of claim 6 wherein the cisplatin compound is selected from the group consisting of:

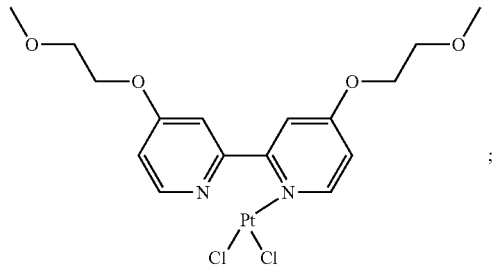

dichloro(4,4'-bis(2-methoxyethoxy)-2,2'-bipyridine)platinum

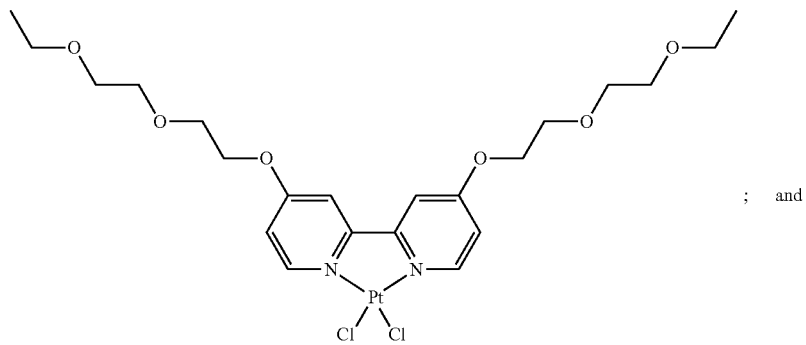

dichloro(4,4'-bis(2-(2-ethoxyethoxy)ethoxy)-2,2'-bipyridine)platinum

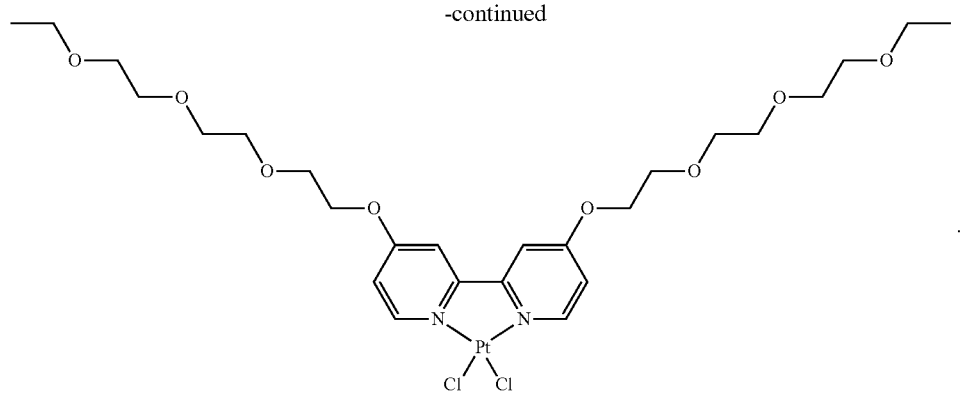
dichloro(4,4'-bis(2-(2-(2-ethoxyethoxy)ethoxy)ethoxy)-2,2'-bipyridine)platinum
* * * * *

UNITED STATES PATENT AND TRADEMARK OFFICE
CERTIFICATE OF CORRECTION

| | | |
|---|---|---|
| PATENT NO. | : 8,703,756 B2 | Page 1 of 1 |
| APPLICATION NO. | : 13/404257 | |
| DATED | : April 22, 2014 | |
| INVENTOR(S) | : Bryan L. Spangelo et al. | |

It is certified that error appears in the above-identified patent and that said Letters Patent is hereby corrected as shown below:

Title Page, Column 1, line 18 (Publications), after "trial" insert -- of --, therefor, In the Claims:

Column 14, line 44 (Claim 4), please delete "C2-C6alkyl" and insert -- C2-C6 alkyl --, therefor, Column 16, line 17 (Claim 15), please delete "the a" and insert -- a --, therefor.

Signed and Sealed this
Twenty-first Day of October, 2014

Michelle K. Lee
*Deputy Director of the United States Patent and Trademark Office*